United States Patent [19]

Tillotson et al.

[11] Patent Number: 5,676,132
[45] Date of Patent: Oct. 14, 1997

[54] PULMONARY INTERFACE SYSTEM

[75] Inventors: Paul J. Tillotson; Thomas T. Taylor, both of Auburn; Timothy R. Tajchman, Seattle; Ronald D. Bingel, Sr., Mount Vernon, all of Wash.

[73] Assignee: Pulmonary Interface, Inc., Redmond, Wash.

[21] Appl. No.: 567,173

[22] Filed: Dec. 5, 1995

[51] Int. Cl.$^6$ .......................................................... A61B 5/08
[52] U.S. Cl. ................... 128/204.23; 128/204.25; 128/207.14; 128/724
[58] Field of Search ...................... 128/204.18, 204.21, 128/205.23, 204.24, 204.25, 207.14, 911, 719, 725, 724

[56] References Cited

U.S. PATENT DOCUMENTS

| | | |
|---|---|---|
| 3,910,261 | 10/1975 | Ragsdale et al. . |
| 4,264,961 | 4/1981 | Nishimura et al. . |
| 4,363,238 | 12/1982 | William . |
| 4,523,461 | 6/1985 | Watkins . |
| 4,571,996 | 2/1986 | Wakeman et al. . |
| 4,604,895 | 8/1986 | Watkins . |
| 4,838,295 | 6/1989 | Smith et al. . |
| 5,038,792 | 8/1991 | Mault .................................. 128/719 |
| 5,081,866 | 1/1992 | Ochiai et al. . |
| 5,355,893 | 10/1994 | Mick et al. ............................ 128/719 |
| 5,413,111 | 5/1995 | Wilkinson ............................. 128/724 |
| 5,460,039 | 10/1995 | Cutler .................................. 73/204.15 |

FOREIGN PATENT DOCUMENTS

173-946-A  3/1986  European Pat. Off. .

Primary Examiner—Vincent Millin
Assistant Examiner—William J. Deane, Jr.
Attorney, Agent, or Firm—Seed and Berry LLP

[57] ABSTRACT

A device for sensing the respiratory air of a patient. The device includes a venturi tube through which the patient inspires and expires, the tube having a constricted midportion. The tube also has an inspiration orifice, an expiration orifice, and a central orifice therebetween. An air mass flow sensor is positioned in the tube. A flow direction housing is attached to the tube and has a channel with an inspiration portion, an expiration portion, and a central portion therebetween. The housing also has an inspiration opening providing communication between the tube inspiration orifice and an end portion of the inspiration channel away from the central channel portion, an expiration opening providing communication between the tube expiration orifice and an end portion of the expiration channel portions away from the central channel portion, and a central opening providing communication between the tube central orifice and the central channel portion. This causes a flow of a portion of the respiratory air which the patient inspires to pass through the tube inspiration orifice and flow through the inspiration channel portion to the housing central opening, and a flow of a portion of the respiratory air which the patient expires to pass through the tube expiration orifice and flow through the expiration channel portion to the housing central opening for return to the venturi tube at the tube constricted portion. A flow direction sensor is positioned in the inspiration channel portion and a flow direction sensor is positioned in the expiration channel portion to produce outputs responsive to the flow of respiratory air through the inspiration and expiration channel portions for determining if the respiratory air flowing through the venturi tube is inspired or expired air.

81 Claims, 6 Drawing Sheets

PULMONARY INTERFACE SYSTEM

TECHNICAL FIELD

This invention relates to a pulmonary interface system, and more particularly to a pulmonary interface system having a respiratory sensing device that measures air mass and volume as well as direction of air flow.

BACKGROUND OF THE INVENTION

It is often necessary or useful to know the amount of air a patient is inspiring or expiring, and there are many applications for a device capable of sensing respiratory air flow. For example, one such application is in the monitoring and control of a ventilating device used by a patient. Other important applications of the respiratory air sensing device include determining the presence of lung disease, as well as determining the cause of the lung disease and a proper course of its treatment. Information obtained from the respiratory air sensing device could also be used to evaluate cardiac rhythms and arrhythmia, or other bodily functions in medical diagnosis. For example, the information from the respiratory air sensing device can be obtained over a given time cycle and/or respiratory sequence, and then compared with standards for a particular age and physical characteristics to determine a patient's health.

Figure 1:
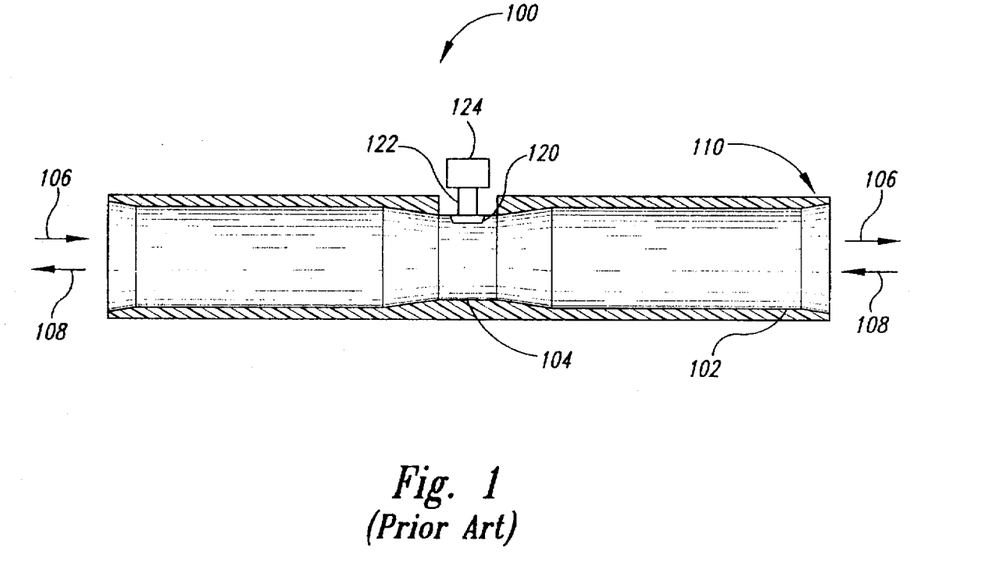
FIG. 1 is a side-sectional view of a prior art conventional respiratory air sensing device.

One type of conventional respiratory air sensing device 100, as shown in FIG. 1, utilizes a venturi-type tube 102 (i.e., having a venturi cross-section) including a midsection area 104 of lesser diameter that offers a resistance to air flow through the tube. The constricted midsection area 104 causes the flow of air that is expired 106 or inspired 108 by a patient at a first end 110 of the venturi-type tube 102 to become a laminar stable air flow in the midsection area 104. A sensor 120, such as a microsensor, is arranged in the midsection area 104 of the venturi-type tube 102, with pins 122 extending outside of the venturi-type tube 102. The sensor 120 protrudes from an inner surface of the venturi-type tube 102 into the laminar air flow, and detects the flow rate of air therethrough. The sensor 120 then sends detection signals to a microprocessor (not shown) via the pins 122 and a connector 124.

The conventional respiratory air sensing device 100 is often bulky and heavy, making it difficult for a patient to maneuver or properly breath through. Further, the conventional respiratory air sensing device 100 is often expensive, and must be re-used by a series of patients, each potentially effected with some form of respiratory disease. This is a source of exceptional concern with the relatively recent appearance of many more types of antibiotic resistant organisms and untreatable viral, bacterial, and fungal respiratory diseases. Thus, to prevent subsequent users of the conventional respiratory air sensing device 100 from being exposed to the respiratory disease of prior users, a competent medical technician must spend an excessive amount of time cleaning and disinfecting the conventional respiratory air sensing device 100 after each use. Disposal of such devices is not economical.

Another disadvantage of the conventional respiratory air sensing device 100 is that its sensor 120 does not provide all the necessary parameters for an accurate reading. For example, temperature, ambient pressure, and air flow direction are not sensed with the conventional respiratory air sensing device 100. Since ambient pressure is not accounted for, and it may vary with altitude and atmospheric conditions, there is no way to ensure that the air flow rate and volume detected by the sensor 120 is accurate. Finally, there is no means to determine the air flow direction to distinguish the inspiration air of a patient from the expiration air of the patient. If a direction indicating device were positioned within the venturi-type tube 102, it would cause air flow turbulence or resistance to flow and interfere with readings made by the sensor 120 and possibly become contaminated by debris in the air flow.

Although the conventional respiratory air sensing device 100 meets most of the diagnostic medical requirements of the past, it no longer provides the accuracy, speed, and sensitivity required by the more advanced diagnostic technologies becoming available to medical science. The present invention fulfills this need and provides other related advantages.

SUMMARY OF THE INVENTION

The present invention resides in a device for sensing direction of flow of a gas, and more specifically, sensing the respiratory air of a patient. The device has a venturi tube including a first open end through which a patient inspires and expires, a second open end, and a constricted portion therebetween. The venturi tube has an inspiration orifice, an expiration orifice, and a central orifice positioned therebetween.

The device also includes an air mass flow sensor positioned within the venturi tube to provide air mass data on the respiratory air flowing through the venturi tube. The device has a conduit with an inspiration portion, an expiration portion, and a central portion therebetween. The conduit has an inspiration opening providing communication between the tube inspiration orifice and an end portion of the inspiration conduit portion spaced away from the central conduit portion. The conduit also has an expiration opening providing communication between the tube expiration orifice and an end portion of the expiration conduit portion spaced away from the central conduit portion. The conduit also includes a central opening providing communication between the tube central orifice and the central conduit portion. With this arrangement, a flow of a portion of the respiratory air which the patient inspires is caused to pass from the second open end of the venturi tube through the tube inspiration orifice and the conduit inspiration opening and flow through the inspiration conduit portion to the conduit central opening and the tube central orifice for return to the venturi tube at the tube constricted portion. Likewise, a flow of a portion of the respirator air which the patient expires is caused to pass from the first open end of the venturi tube through the tube expiration orifice and the conduit expiration opening and flow through the expiration conduit portion to the conduit central opening and the tube central orifice for return to the venturi tube at the tube constricted portion.

The device has an inspiration air flow direction sensor positioned in the inspiration conduit portion which provides an output responsive to the flow of the portion of the respiratory air through the inspiration conduit portion. The device also has an expiration air flow direction sensor positioned in the expiration conduit portion which has an output responsive to the flow of the portion of the respiratory air through the expiration conduit portion. With this arrangement, the respiratory air flowing through the venturi tube can be determined to be inspired air or expired air from the outputs of the inspiration and expiration air flow direction sensors.

In the preferred embodiment of the invention, the inspiration flow direction sensor provides an expiration temperature signal, and the expiration air flow direction sensor provides an inspiration temperature signal. The expiration and inspiration temperature signals are indicative of whether the respiratory air flow through the venturi tube is inspired or expired air.

In a preferred embodiment, an electronic device is electronically coupled to the expiration flow direction sensor and the inspiration flow direction sensor to use the inspiration temperature signal and the expiration temperature signal to determine whether the respiratory air flowing through the venturi tube is inspired or expired air.

In the preferred embodiment the flow sensor is an air mass sensor that produces an air mass indication signal. The device also includes an air temperature sensor positioned within the venturi tube to produce an air temperature indication signal. The device further includes a humidity sensor to detect the humidity of the ambient air outside of the venturi tube and produce a humidity indication signal, and a pressure sensor to detect the pressure of the ambient air outside the venturi tube and produce a pressure indication signal. The electronic device is electronically coupled to the flow sensor, the air temperature sensor, the humidity sensor and the pressure sensor to use the air mass indication signal, the temperature indication signal, the humidity indication signal, and the pressure indication signal to determine the volume of the respiratory air flowing through the venturi tube.

The flow sensor is held in position within the venturi tube by a plug positioned in the conduit central opening. The plug has an air passage therethrough communicating with the central conduit portion and the tube constricted portion.

The device further includes a housing with an outward housing portion and an inward housing portion. The outward housing portion has a channel formed on an inward face thereof to define the conduit. The inward housing portion is positioned between the venturi tube and the outward housing portion. The inward housing portion has an inward face and an outward face with the conduit inspiration opening, the conduit expiration opening and the conduit central opening extending fully between the inward and outward faces of the inward housing portion. The inward face of the inward housing portion is sealingly mounted to the venturi tube and the outward housing portion has the inward face thereof sealingly mounted to the outward face of the inward housing portion with the channel overlaying the conduit inspiration, expiration and central openings of the inward housing portion. The plug is sealingly mounted in the conduit central opening of the inward housing portion and sealingly engages the venturi tube about the tube central orifice to provide a seal between the venturi tube and the inward housing portion.

The present invention can also be embodied in a gas flow sensing device using a single side channel or conduit extending between an orifice toward one end of the venturi tube and a central orifice at a constricted portion of the venturi tube to cause a portion of the gas flowing in one direction in the venturi tube to pass through the tube end orifice into the conduit and out the central orifice to the tube constricted portion to sense the flow of gas in the conduit and thereby determine the direction of gas flow in the venturi tube in a first direction. A gas mass flow sensor positioned in the venturi tube detects flow of gas therethrough without regard to direction. An electronic device determines that gas is flowing in the venturi tube in a second direction based on the lack of an indication of flow in the conduit and the presence of a flow in the venturi tube.

In an alternative embodiment, the respiratory air sensing device includes a sample container in communication with the conduit to allow a flow of a portion of the respiratory air in the conduit into the sample container.

In yet other alternative embodiments, the respiratory air sensing device is used with a flexible tube portion and positioned within the trachea of a patient.

Other features and advantages of the invention will become apparent from the following detailed description, taken in conjunction with the accompanying drawings.

DETAILED DESCRIPTION OF THE INVENTION

Figure 2:
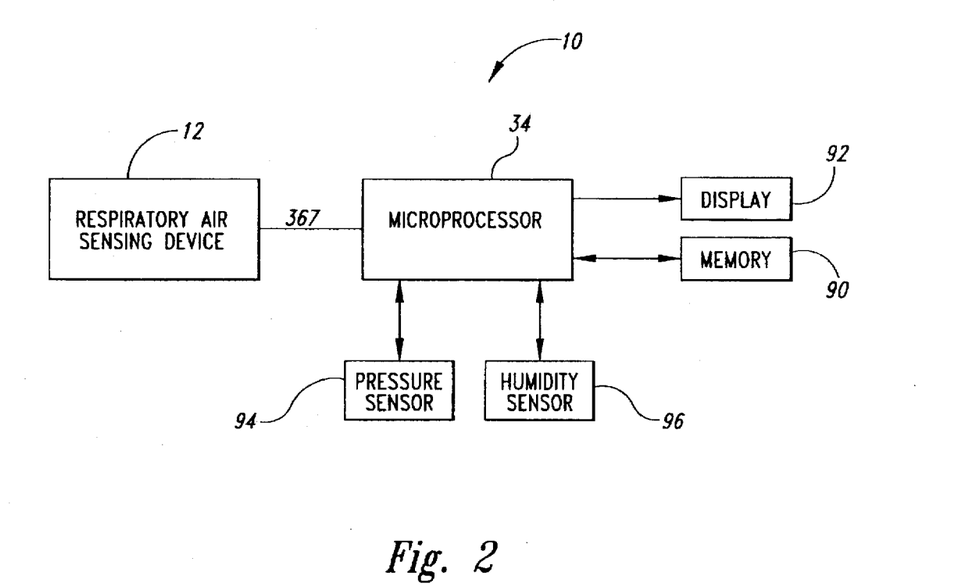
FIG. 2 is a block diagram schematic of a pulmonary interface system of the present invention which includes a respiratory air sensing device.
Figure 3:
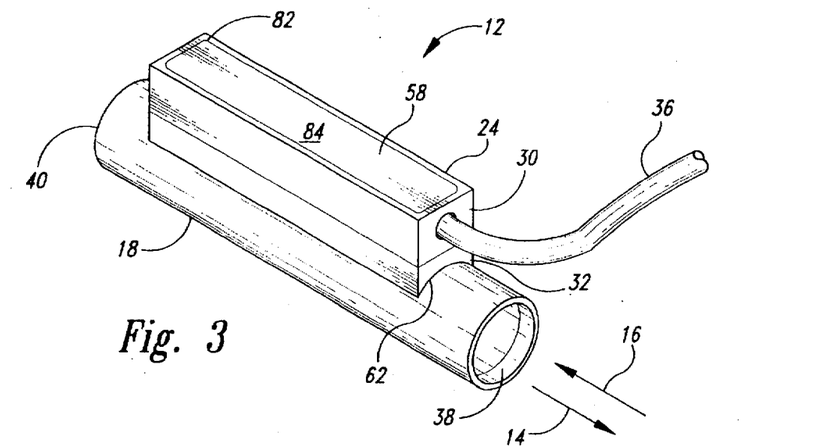
FIG. 3 is an isometric view of the respiratory air sensing device of FIG. 2.

The present invention is embodied in a pulmonary interface system 10, shown in FIG. 2, having a disposable respiratory air sensing device 12 for determining the volume of air inspired, illustrated by arrow 14, and air expired, illustrated by arrow 16, from a patient, in a rapid and highly precise manner. The respiratory air sensing device 12 is illustrated in FIG. 3 fully assembled but separated from the other components that comprise the pulmonary interface system 10.

Figure 4:
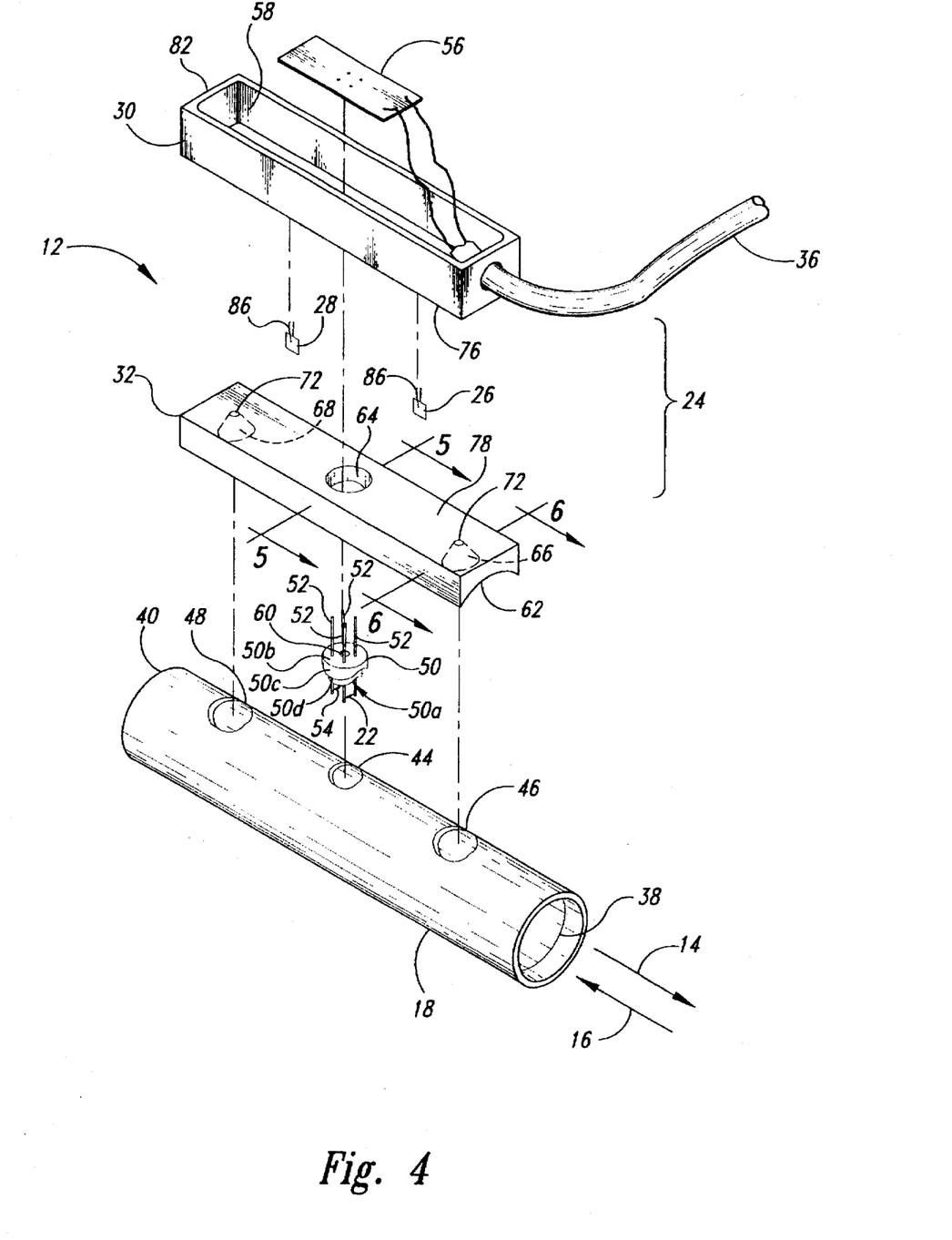
FIG. 4 is an exploded view of the respiratory air sensing device of FIG. 3.
Figure 5:
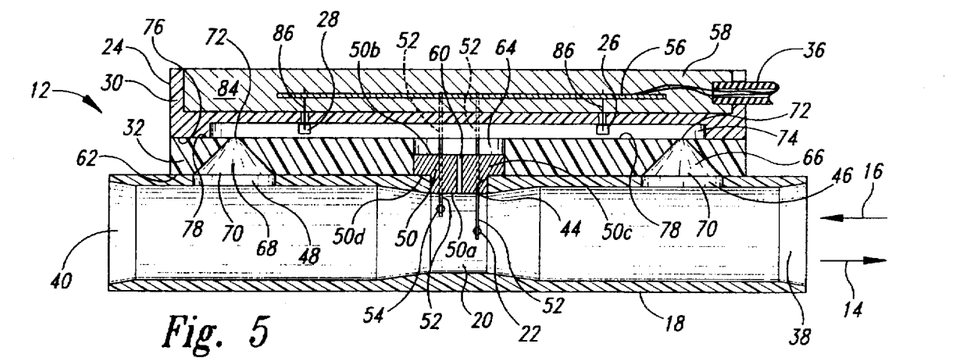
FIG. 5 is an enlarged, side-sectional view of the respiratory air sensing device of FIG. 3.

As best shown in FIGS. 4 and 5, the respiratory air sensing device 12 includes a rigid venturi tube 18 having a midportion 20 with a constricted, venturi-shaped central cross-section for facilitating a laminar flow of air within at increased speed and lower pressure. The interior diameter of the venturi tube 18, other than at the midportion 20, is sized to approximate the average size of the tracheal tube of the typical patient. A hot-wire anemometer 22 is positioned in the midportion 20 of the venturi tube 18 to detect the mass of air passing therethrough. The respiratory air sensing device 12 also includes a flow direction indicator housing 24 used in detecting the direction of air flow within the venturi tube 18 without risking contamination of an expiration thermistor 26 and an inspiration thermistor 28 positioned therein from debris within the air flow of the venturi tube 18, such as mucous, blood clots and the other matter. By use of the flow direction indicator housing 24 the direction of air flow is detected without causing turbulence within the venturi tube 18 that might interfere with the accurate measurement of the mass of air detected by the hot-wire anemometer 22. The flow direction indicator housing 24 includes an outward housing portion 30 and an inward housing portion 32. The inward housing portion 32 is mounted directly on the venturi tube 18 and the outward housing portion 30 is mounted on the inward housing portion, as will be described in greater detail below. Electrical signals sent by the hot-wire anemometer 22, as well as the expiration and inspiration thermistors 26 and 28 in the flow direction indicator housing 24 are sent to an external microprocessor 34 (see FIG. 9) via an electrical cable 36 attached to the flow direction indicator housing. As will be described below, the inexpensive construction of the venturi tube 18 and the flow direction indicator housing 24 allows for its economical disposal after each use. The entire respiratory air sensing device 12 shown in FIG. 3, except for the cable 36 which is detachable by a connector (not shown), is disposable, to avoid reuse of the portions that come into contact with the patient airway.

An exploded view of the respiratory air sensing device 12 is shown in FIG. 4 and illustrates the inexpensive construction used which allows the device to be disposed after each use, thereby eliminating any chance of transmitting a respiratory borne disease from one patient to another. More specifically, the venturi tube 18 includes a first end opening 38 into which a patient breathes and a second end opening 40 which is either open to the environment or connected to a ventilating device 42 (see FIG. 9). The venturi tube 18 has a central orifice 44 at the location of the midportion 20 thereof in a position substantially centered between the first and second end openings 38 and 40. The venturi tube 18 also has an expiration orifice 46 and an inspiration orifice 48 positioned along the length thereof in a substantially linear arrangement with the central orifice 44. The central orifice 44, the expiration orifice 46 and the inspiration orifice 48 are on a side of the venturi tube 18 at which the inward housing portion 32 is positioned on the venturi tube, and the inward housing portion is elongated to fully overlay all three orifices. The expiration and inspiration orifices 46 and 48 are spaced at approximately equidistant positions from the central orifice 44, with the expiration orifice 46 being toward the first end opening 38 and the inspiration orifice 48 being toward the second end opening 40.

The central orifice 44 is sized to snugly receive a sensor plug 50, which has embedded therein four electrically conductive posts 52. The posts 52 project inward from an inward end 50a of the sensor plug 50 into the midportion 20 of the venturi tube 18, with two posts supporting and electrically connected to the hot-wire anemometer 22, and two posts supporting and electrically connected to a temperature detector 54. When seated in the central orifice 44 of the venturi tube 18, the inward end 50a of the sensor plug 50 is flush with an inner wall of the venturi tube 18, with only the posts 52 and the hot-wire anemometer 22 and temperature detector 54 they support extending into the interior of the midportion 20 of the venturi tube 18 in the flow of air passing therethrough. The posts 52 project outward from an outward end 50b of the sensor plug 50 and are electrically connected to a circuit board 56 positioned within an outward opening compartment 58 of the outward housing portion 30 of the flow direction indicator housing 24. The sensor plug 50 has an axially extending air passage 60 extending between the inward end 50a and outward end 50b of the plug 50 to allow air to pass therethrough. The inward end of the air passage 60 communicates with the midportion 20 of the venturi tube 18.

Figure 6:
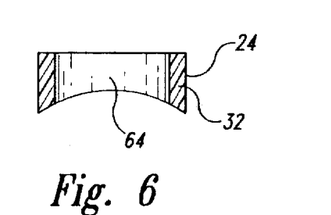
FIG. 6 is a cross-sectional view of a central aperture of an adapter of the respiratory air sensing device substantially taken along lines 5—5 of FIG. 4.

The inward housing portion 32 of the flow direction indicator housing 24 has a concave inward side 62 which is shaped to be seated on and match the contour of the exterior wall of the venturi tube 18. The inward housing portion 32 has a cylindrical central aperture 64, illustrated in FIG. 6, sized to snugly receive therein a cylindrical upper portion 50c of the sensor plug 50 which is outward of the central orifice 44 and is larger in diameter than the central orifice 44. An inward annular edge portion 50d of the upper portion 50c of the sensor plug 50 is shaped to contact and form an airtight fit with the exterior wall of the venturi tube 18 about the central orifice 44 such that air flow between the central aperture 64 outward of the sensor plug 50 and the venturi midportion 20 of the venturi tube passes only through the air passage 60 in the sensor plug.

Figure 7:
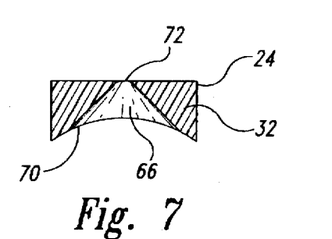
FIG. 7 is a cross-sectional view of an end aperture of the adapter of the respiratory air sensing device substantially taken along lines 6—6 of FIG. 4.

The inward housing portion 32 also includes an expiration aperture 66 positioned toward an end thereof toward the first end opening 38 of the venturi tube 18, and an inspiration aperture 68 positioned toward an end thereof toward the second end opening 40 of the venturi tube. The expiration and inspiration end apertures 66 and 68 are positioned along the length of the inward housing portion 32 in substantially linear arrangement with the central aperture 64, and are spaced at approximately equidistant positions from the central aperture 64 in coaxial alignment with the expiration and inspiration orifices 46 and 48, respectively, of the venturi tube 18. The expiration and inspiration apertures 66 and 68 are each conical in shape, as best shown in FIG. 7 for the expiration aperture 66, and have a wide inward opening 70 aligned with the corresponding one of the expiration and inspiration orifices 46 and 48 of the venturi tube 18. The expiration and inspiration apertures 66 and 68 each have a narrow outward opening 72 which communicates with an elongated channel 74 formed the outward housing portion 30 of the flow direction indicator housing 24. The conical or "funnel shape" of the expiration and inspiration apertures 66 and 68 significantly reduces clogging due to particulate matter in the air flowing therethrough.

As will be described in detail below, the air flow through the expiration and inspiration apertures 66 and 68 is always in the direction from the expiration and inspiration orifices 46 and 48, respectively, of the venturi tube 18 through the wide inward opening 70 to the narrow outward opening 72 of the expiration and inspiration apertures, and then to the channel 74. This results in any debris (e.g., mucous, blood clots) in the air flow in the venturi tube 18 that might tend to enter the expiration or inspiration apertures 66 and 68 doing so from its wide inward opening 70 to its narrow outward opening 72, thus significantly diminishing the chances of blockage resulting.

Figure 8:
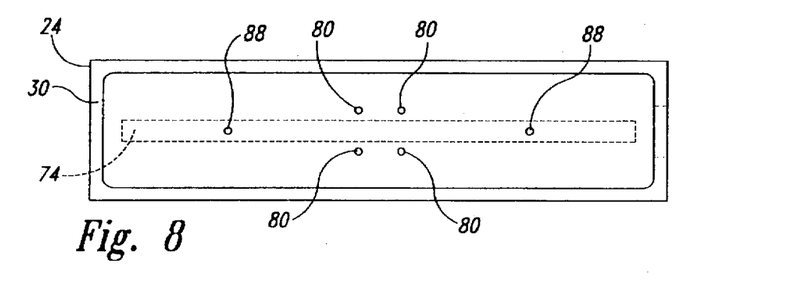
FIG. 8 is an enlarged, top view of the flow direction indicator housing of the respiratory air sensing device of FIG. 4 shown disassembled from the adapter.

The channel 74 is formed using an elongated, closed end groove in a planar inward side 76 of the outward housing portion 30, and sealing the planar inward side 76 against a planar outward side 78 of the inward housing portion 32. As shown in FIG. 8, the outward housing portion 30 has four apertures 80 sized to receive the four posts 52. The post apertures 80 are positioned laterally outward of the channel 74 so as not to communicate with the channel. An outward side 82 of the outward housing portion 30 has the compartment 58 formed therein which as noted above holds the circuit board 56. The post apertures 80 communicate with the compartment 58 and the posts 52 extend out of the post apertures into the compartment where they are electrically connected to the circuit board 56. The circuit board 56 is securely retained in the compartment 58 by epoxy 84 which fills the compartment and encases the circuit board.

The expiration thermistor 26 is positioned within the channel 74 toward an end portion thereof toward the first end opening 38 of the venturi tube 18, between the locations where the central aperture 64 and the expiration aperture 66 of the inward housing portion 32 communicate with the channel 74. The inspiration thermistor 28 is positioned within the channel 74 toward an end portion thereof toward the second end opening 40 of the venturi tube 18, between the locations where the central aperture 64 and the inspiration aperture 68 of the inward housing portion 32 communicate with the channel 74. While the expiration and inspiration thermistors 26 and 28 are positioned within the channel 74, they are sized not to fully block the channel, which is of much smaller size than the interior diameter of the venturi tube 18. The expiration and inspiration thermistors 26 and 28 have electrical leads 86 by which they are held fixed in position in the channel 74 and electrically connected to the circuit board 56. As shown in FIG. 8, the outward housing portion 30 of the flow direction indicator housing 24 has a pair of apertures 88 extending between the channel 74 and the compartment 58 through which the leads 86 of the expiration and inspiration thermistors 26 and 28 pass. The epoxy 84 which fills the compartment 58 seals the lead apertures 88 about the leads 86.

When the air flow within the venturi tube 18 is in the direction of arrow 16 as occurs on expiration or in the direction of arrow 14 as occurs on inspiration, a reduced pressure is produced in the midportion 20 of venturi tube 18 at the inward end of the air passage 60 of the sensor plug 50. This reduced pressure creates an air flow in the channel 74, with the direction being from the expiration aperture 66 to the central aperture 64 and through the air passage 60 on expiration (arrow 16), and with the direction being from the inspiration aperture 68 to the central aperture 64 and through the air passage 60 on inspiration (arrow 14). When expiration (arrow 16) takes place a larger air flow occurs in a portion of the channel 74 in which the expiration thermistor 26 is positioned, and thus the air flow past the expiration thermistor 26 is greater than the air flow past the inspiration thermistor 28, and when inspiration (arrow 14) takes place a larger air flow occurs in a portion of the channel 74 in which the inspiration thermistor 28 is positioned, and thus the air flow past the inspiration thermistor 28 is greater than the air flow past the expiration thermistor 26. The expiration and inspiration thermistors 26 and 28 are self-heated thermistors, and by comparing the measured flow rates past each thermistor, based on the observed temperature signals emitted by the thermistors, it is possible to determine with high speed and accuracy whether the air flow rate is larger past the expiration thermistor 26 or the inspiration thermistor 28, and hence the direction of the air flow within the venturi tube 18. This identifies whether the air flow is expired air or inspired air. Because the expiration and inspiration thermistors 26 and 28 are located in the channel 74 instead of the venturi tube 18, they create no turbulence in the venturi tube which might cause an erroneous reading by the hot-wire anemometer 22. Further, there is little chance of debris entering the channel 74 from the venturi tube 18 to cause erroneous readings by the expiration and inspiration thermistors.

By knowing whether the volume of air being measured at a particular moment as it passes through the venturi tube 18 is expired or inspired air, the measurement is more useful in testing and evaluating the pulmonary/respiratory function of the patient. When using the respiratory air sensing device 12 to accomplish metabolic analysis, such as when sampling of the respiration for disease, oxygen content, alcohol presence or various metabolite by-products, such as carbon dioxide, it is important to know if the air being sampled is being exhausted from the lung of the patient (during expiration) or if the air being sampled is ambient air being drawn into the lung (during inspiration). When using the respiratory air sensing device 12 to monitor and analyze lung and other respiratory and cardiac functions, it is also important to distinguish the expired air from inspired air. With the respiratory air sensing device 12 the volumetric measurements taken can be plotted as a function of time and used to depict performance characteristics of the lung and the respiratory and cardiac systems of the patient. It is fundamental that the portion of such a plot that represents expiration must be distinguishable from the portion that represents inspiration for meaningful analysis and diagnosis to occur.

Figure 9:
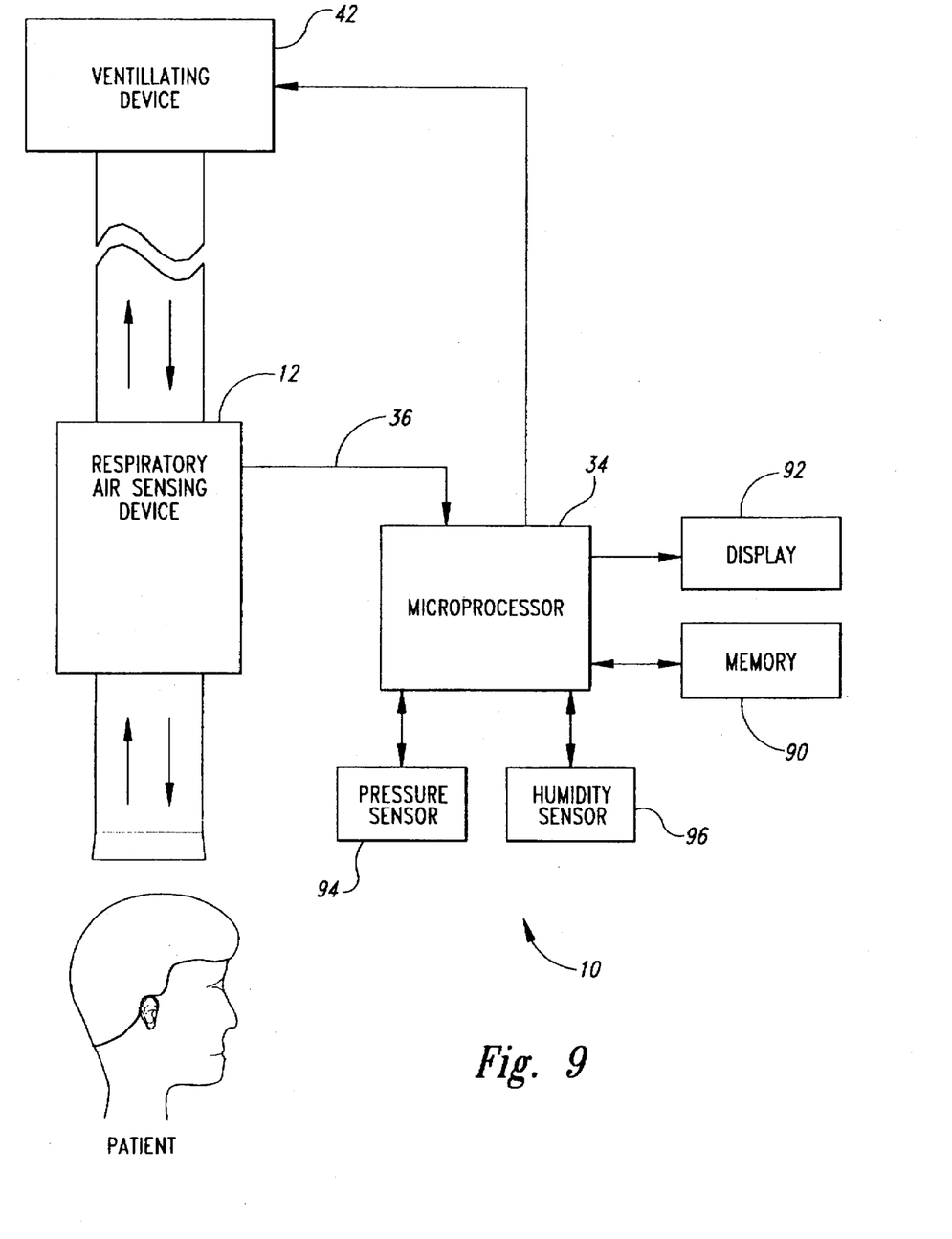
FIG. 9 is a block diagram schematic of the pulmonary interface system of FIG. 2 used with a ventilating device.

In operation, as illustrated in FIG. 9, the microprocessor 34 compares temperature change signals from the expiration thermistor 26 and the inspiration thermistor 28, sent via the cable 36, and thereby determines the direction of the air flow in the venturi tube 18. This information is then stored in a memory 90 or displayed to a medical technician on a display 92, or both. The microprocessor 34, the memory 90 and the display 92 are external to the venturi tube 18 and the flow direction indicator housing 24, and separable from the respiratory air sensing device 12 they form so as to allow for economical disposal of the respiratory air sensing device.

The pulmonary interface system 10, shown in FIG. 9, is capable of making high speed, highly precise and accurate reading of respiratory air flow volume by directly and automatically monitoring parameters never before taken into account by respiration monitors, such as ambient pressure. To determine the volume of air flow through the venturi tube 18 with accuracy, an air mass reading is taken by the hot-wire anemometer 22. Further, the internal temperature of the venturi tube 18 (i.e., the air passing through the venturi tube) is monitored by the temperature detector 54. These values are processed by additional circuitry and the microprocessor 34 using methods well known in the art. Ambient air pressure is monitored with a pressure sensor 94, and ambient humidity is monitored with a humidity sensor 96. These ambient sensors are separate from the respiratory air sensing device 12 to allow for economical disposal of the device. If they were incorporated into the respiratory air sensing device 12, a system of valves must be used to protect the sensors from the device's internal conditions.

The microprocessor 34 receives an air mass indicator signal from the hot-wire anemometer 22, a temperature indicating signal from the temperature detector 54, a pressure signal from the pressure sensor 94, and a humidity signal from the humidity sensor 96. The microprocessor 34 analyzes these signals and makes the necessary corrections for ambient pressure and humidity and outputs an information signal relating the amount of air flow in the venturi tube 18 either to an external computer (not shown) or directly to the display 92 and/or memory 90. No manual entry of the ambient air pressure is needed so the respiratory air sensing device 12 is easier to use and avoids user data input errors.

As described above, the microprocessor 34 also determines the direction of air flow in the venturi tube 18. This direction determines whether the microprocessor 34 will calculate the actual amount of air flow through the venturi tube 18 using ambient humidity in its calculation (during an inspiration) or automatically use a humidity value of 100% (during an expiration, since expirations almost always contain enough moisture to produce a reading of 100% humidity). A direction signal based on the direction of air flow in the venturi tube 18 is also sent by the microprocessor 34 to a computer (not shown) or directly to the display 92 and/or the memory 90.

During expiration, the internal temperature of the venturi tube 18 monitored by the temperature detector 54 is a function of the temperature of the expired air of the patient using the respiratory air sensing device 12. The temperature of the expired air is believed to be indicative of the body core temperature of the patient. The body core temperature information is a critical vital sign and is extremely useful to diagnose hypothermia, hyperthermia, entry into shock, and other conditions. As such, the temperature indicating signal received by the microprocessor from the temperature detector 54 is processed and converted to a body core temperature, which temperature is then stored in the memory 90 and displayed to a physician or medical technician on the display 92. As described, the microprocessor 34 determines the direction of air flow in the venturi tube 18, hence the microprocessor can distinguish measured temperatures of expired air from inspired air, and avoid erroneously determining and displaying body core temperature based on inspired air since the temperature of inspired air is simply representative of the ambient air temperature.

The respiratory air sensing device 12 has been described using expiration thermistor 26 and inspiration thermistor 28 to detect the flow direction of air in the channel 74 and hence the venturi tube 18 in both directions. However, the respiratory air sensing device 12 can be manufactured using only one of the expiration and inspiration thermistors, or one of the thermistors may fail or be rendered inoperative by a clog in the channel 74, but yet the device can still determine flow in two directions. For example, if only the expiration thermistor 26 is operative or even used, it senses flow in the channel 74 and hence the venturi tube 18 in only the expiration direction indicated by arrow 16 in FIGS. 3, 4 and 5. The flow in the inspiration direction indicated by arrow 14 can still be detected because the existence of air flow in any direction in the venturi tube 14 is detected by the hot-wire anenometer 22, although without any indication of the direction of the flow. The fact that flow is occurring in the inspiration direction can be determined by the microprocessor 34 by the presence of the air mass signal from the hot-wire anenometer 22 and the lack of any temperature emitted by the expiration thermistor 26. Flow in the reverse direction can be also determined if the inspiration thermistor 26 is used but has failed or is rendered inoperative by a clog. In effect, by utilizing both the expiration and inspiration thermistors 26 and 28, the respiratory air sensing device 12 has redundancy built in should one of the thermistors fail or a clog occur. Alternatively, one of the thermistors can be detected to produce a less expensive device, but yet flow in both directions can still be detected.

In one embodiment, the pulmonary interface system 10 can be used in conjunction with a ventilating device 42, such as a respirator, as shown in FIG. 9. The output of the ventilating device 42 is monitored by the respiratory sensing device 12 and the resulting information is placed in the memory 90 and/or displayed to a medical technician on the display 92. In a preferred embodiment, the information and directional signals from the microprocessor 34 can be sent to the ventilating device 42, via the computer (not shown) to regulate its output based on a patient's monitored use.

Figure 10:
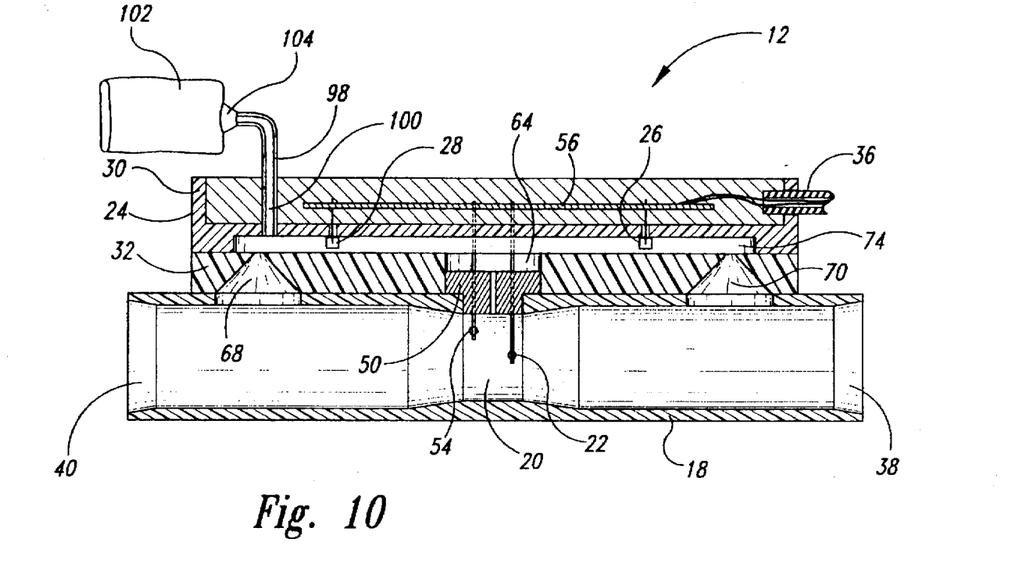
FIG. 10 is a side-sectional view of an alternative embodiment of the respiratory air sensing device of the present invention which allows the retrieval of respiratory air samples.

FIG. 10 shows an alternative embodiment of the present invention. The respiratory air sensing device 12 further includes a tube 98 that is coupled to a passageway 100 in communication with the channel 74. A sample container 102 is detachably coupled via a one-way fitting 104 to the tube 98 to allow a physician or medical technician to take a sample of the breath of a patient in a manner free of any contaminants. The sample can be used for analysis by other known devices to determine its gaseous composition and content.

Figure 11:
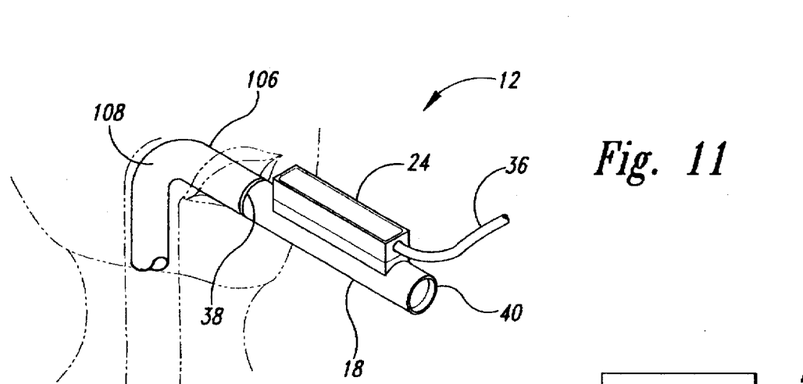
FIG. 11 is an isometric view of a second alternative embodiment of the respiratory air sensing device of the present invention shown in use.

A second alternative embodiment of the present invention is shown in FIG. 11. The respiratory air sensing device 12 has a flexible tube 106 removably fitted onto the venturi tube 18 at the first end opening 38. The flexible tube 106 has sufficient flexibility to be bent along a portion 108 thereof to accommodate the normal curvature of the respiratory passageway during insertion through the mouth and into the trachea, and to permit easy removal. The venturi tube 18 and the flexible tube 106 are of reduced diameter for use with neonatal patients having small trachea.

Figure 12:
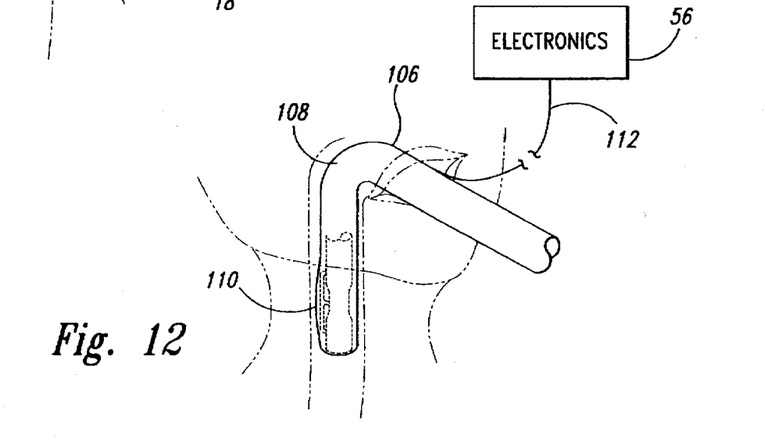
FIG. 12 is an isometric view of a third alternative embodiment of the respiratory air sensing device of the present invention shown in use.

A third alternative embodiment of the present invention is shown in FIG. 12. The flexible tube 106 is manufactured integral with the venturi tube although the portion forming the venturi tube is somewhat stiff to maintain the venturi shape at the midportion 20. The flow direction housing which contains the channel 74 is either manufactured in a reduced size or, as shown in FIG. 12, found in a thick wall portion 110 of the wall of the venturi tube 18 to facilitate insertion of the end of tube with the channel 74 into the trachea to take the expiration measurement before the expired air reaches the bent portion 108 of the tube to avoid the measurement being affected by air turbulence that might occur in the bent portion. With this arrangement, the electronics on the circuit board 56 are positioned separate from the flow direction housing to reduce the housing size and positioned exterior of the patient with the electrical signal emitted being conducted to the circuit board 56 by a thin wire 112.

Figure 13:
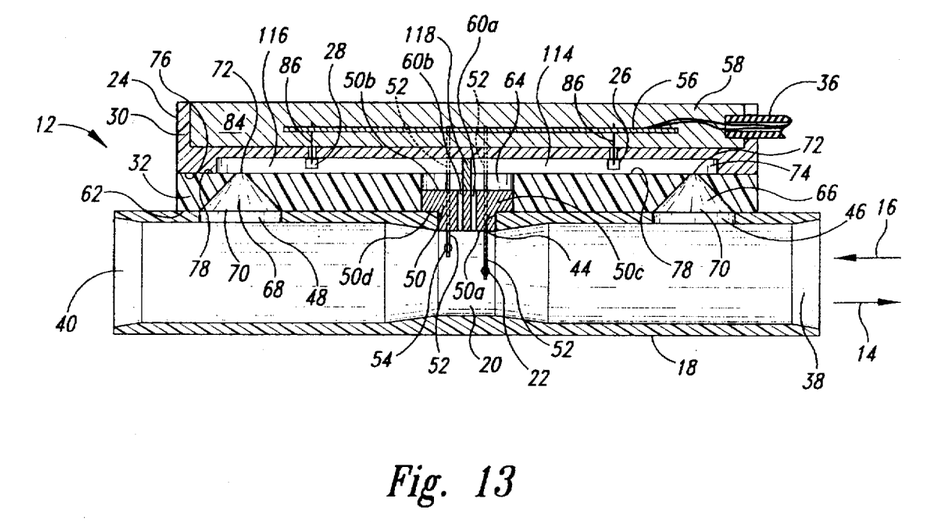
FIG. 13 is a side-sectional view of a fourth alternative embodiment of the respiratory air sensing device of the present invention.

A fourth alternative embodiment of the present invention is shown in FIG. 13. In this embodiment the respiratory air sensing device 12, the channel 74 is divided into an expiration portion 114 and an inspiration portion 116 by a center dividing wall 118 positioned in the central aperture 64 and extending between the outward end 50b of the sensor plug 50 and an outward wall of the channel 74. The center wall 118 sealably engages the sensor plug 50, and the outward and inward housing portions 30 and 32 so as to form two center channel portions for the channel 74 which each communicate with the midportion 20 of the venturi tube 18. The center wall 118 separates the flows in the expiration channel portion 114 and the inspiration channel portion 116 from each other, and the sensor plug 50 has two air passages, an expiration air passage 60a which communicates the expiration channel portion 114 with the midportion 20 of the venturi tube 18, and an inspiration air passage 60b which communicates the inspiration channel portion 116 with the midportion 20 of the venturi tube. Except for the separation of the flows, the respiratory air sensing device 12 of FIG. 13 operates as described above.

Figure 14:
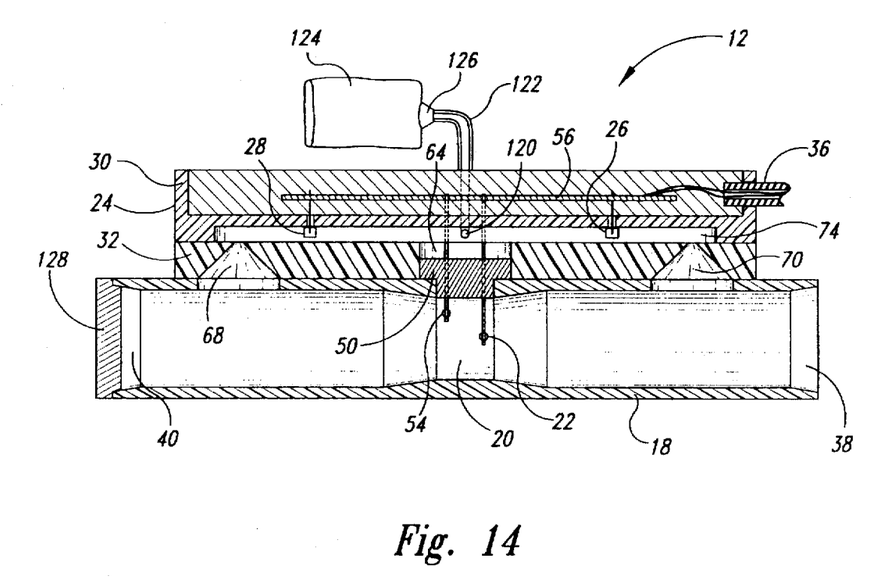
FIG. 14 is a side-sectional view of a fifth alternative embodiment of the respiratory air sensing device of the present invention.

A fifth alternative embodiment of the present invention is shown in FIG. 14 which utilizes a sensor plug 50 without the air passage 60. Instead, the central portion of the channel 74 communicates with the exterior of the flow direction indicator housing 24, at a location outside of the venturi tube 18, through a conduit 120 formed in a sidewall portion of the outward housing portion 30. In the embodiment of FIG. 14, the conduit 120 is shown connected by a tube 122 to a sample container 124 via a one-way fitting 126 to allow a physician or medical technician to take a sample of the breath of a patient. The constricted midportion 20 of the venturi tube 18 will cause pressure within the venturi tube to build when a patient expires air into the first end opening 38 of the venturi tube, or inspires air into the second end opening 40 of the venturi tube. This will cause a flow of air through the channel 74, much as described above except the air path is to the outside of the venturi tube instead of into the midportion 20 thereof. To insure sufficient pressure is built up inside the venturi tube 18 during expiration to force air through the channel 74 and out of the conduit 120, especially when the sample container 124 is used to take an air sample of the patient's expired breath, a removable end cap 128 can be momentarily positioned to at least partially close the second end opening 40 of the venturi tube. Alternatively, the hand of the patient may be used to partially close the second end opening 40.

Accordingly, the present invention allows rapid and accurate measurements of the volume of a patient's respiration by using more parameters. Additionally, the respiratory air sensing device 12 is inexpensive and easy to construct allowing it to be economically disposed after a patient's use. Finally, the present invention may be used to acquire respiratory samples and determine the direction of a respiratory air flow without interfering with the sensors used to determine the amount of the air flow.

Except as otherwise disclosed herein, the various components shown in outline or block form are individually well known and their internal construction and their operation is not critical either to the making or the using of the present invention or to a description of the best mode of the present invention.

While the detailed description above has been expressed in terms of specific examples, those skilled in the art will appreciate that many other structures could be used to accomplish the purpose of the present invention. Accordingly, it can be appreciated that various modifications of the above-described embodiments may be made without departing from the spirit and scope of the present invention. Therefore, the spirit and scope of the present invention are to be limited only by the following claims.

We claim:

1. A device for sensing the respiratory air of a patient, comprising:

a venturi tube including a first open end through which the patient inspires and expires, a second open end, and a constricted midportion therebetween, said venturi tube having an inspiration orifice, an expiration orifice, and a central orifice positioned therebetween at said tube midportion;

a flow sensor positioned within said tube midportion to provide air flow data on the respiratory air flowing through said venturi tube;

a flow direction housing attached to said venturi tube exterior thereof, said housing having a channel with an inspiration portion, an expiration portion and a central portion positioned therebetween, said housing further including an inspiration opening aligned with said tube inspiration orifice and in communication with an end portion of said inspiration channel portion spaced away from said central channel portion, an expiration opening aligned with said tube expiration orifice and in communication with an end portion of said expiration channel portion spaced away from said central channel portion, and a central opening aligned with said tube central orifice and in communication with said central channel portion to cause a flow of a portion of the respiratory air which the patient inspires to pass from said second open end of said venturi tube through said tube inspiration orifice and said housing inspiration opening and to flow through said inspiration channel portion to said housing central opening and said tube central orifice for return to said venturi tube at said tube midportion, and a flow of a portion of the respiratory air which the patient expires to pass from said first open end of said venturi tube through said tube expiration orifice and said housing expiration opening and to flow through said expiration channel portion to said housing central opening and said tube central orifice for return to said venturi tube at said tube midportion; and an inspiration air flow direction sensor positioned in said inspiration channel portion and having an output responsive to said flow of said portion of the respiratory air through said inspiration channel portion, and an expiration air flow direction sensor positioned in said expiration channel portion and having an output responsive to said flow of said portion of the respiratory air through said expiration channel portion, wherein the respiratory air flowing through said venturi tube can be determined to be inspired air or expired air by comparing said outputs of said inspiration and expiration air flow direction sensors.

2. The respiratory air sensing device according to claim 1 wherein said inspiration air flow direction sensor is a thermistor positioned in said inspiration channel portion and providing an inspiration temperature signal, and said expiration air flow direction sensor is a thermistor positioned in said expiration channel portion and providing an expiration temperature signal, and wherein the signal strength of said inspiration temperature signal relative to the signal strength of said expiration temperature signal is indicative of whether the respiratory air flowing through said venturi tube is inspired or expired air.

3. The respiratory air sensing device according to claim 2 wherein said flow sensor positioned within said tube midportion is an air mass sensor that produces an air mass indication signal.

4. The respiratory air sensing device according to claim 3 further including an air temperature sensor positioned within said tube midportion to produce an air temperature indication signal.

5. The respiratory air sensing device according to claim 4 further including a circuit board supported by said housing and electrically coupled to said air mass sensor, said air temperature sensor, said expiration thermistor and said inspiration thermistor.

6. The respiratory air sensing device according to claim 5, further including a microprocessor electrically coupled to said circuit board to compare the signal strength of said inspiration temperature signal with the signal strength of said expiration temperature signal to determine whether the respiratory air flowing through said venturi tube is inspired or expired air.

7. The respiratory air sensing device according to claim 6, further including a humidity sensor to detect the humidity of the ambient air outside said venturi tube and produce a humidity indication signal, and a pressure sensor to detect the pressure of the ambient air outside said venturi tube and produce a pressure indication signal, said microprocessor receiving and using said air mass indication signal, said temperature indication signal, said humidity indication signal and said pressure indication signal to determine the volume of said respiratory air flowing through said venturi tube.

8. The respiratory air sensing device according to claim 6 for use with a ventilating device, wherein said second open end of said venturi tube is connected to the ventilating device, and said microprocessor outputs a signal to the ventilating device to control an amount of air produced by the ventilating device and supplied to said second open end of said venturi tube based on the volume of said respiratory air determined by said microprocessor to be flowing through said venturi tube.

9. The respiratory air sensing device according to claim 1 wherein said flow sensor is held in position within said tube midportion by a plug, said plug being positioned in said tube central orifice and said housing central opening, and has an air passage therethrough communicating with said central channel portion and said tube midportion.

10. The respiratory air sensing device according to claim 9 wherein said plug is sealingly mounted in said tube central orifice and said housing central orifice to provide a seal between said venturi tube and said housing.

11. The respiratory air sensing device according to claim 9, wherein said housing includes an outward housing portion having said channel formed on an inward face thereof, and an inward housing portion positioned between said venturi tube and said outward housing portion, said inward housing portion having an inward face and an outward face with said housing inspiration opening, said housing expiration opening and said housing central opening extending fully between said inward and outward faces of said inward housing portion, said inward housing portion having said inward face thereof sealingly mounted to said venturi tube and said outward housing portion having said inward face thereof sealingly mounted to said outward face of said inward housing portion with said channel overlaying said housing inspiration, expiration and central openings of said inward housing portion.

12. The respiratory air sensing device according to claim 11 wherein said housing inspiration opening and said housing expiration openings of said inward housing portion are tapered having a first portion thereof toward said venturi tube for communication with said tube inspiration and expiration orifices, and a second portion thereof narrower than said first portion toward said outward face of said inward housing portion for communication with said channel.

13. The respiratory air sensing device according to claim 11 further including a circuit board electrically coupled to said flow sensor, and said inspiration and expiration air flow direction sensors, and wherein said outward housing portion has a chamber formed in an outward face thereof, outward of said channel, sized to received said circuit board therein.

14. The respiratory air sensing device according to claim 1 further including a sample container and a conduit coupling said sample container to said channel to allow a flow of a portion of said respiratory air in said channel into said sample container.

15. A device for sensing the respiratory air of a patient, comprising:

a venturi tube including a first open end through which the patient inspires and expires, a second open end, and a constricted portion therebetween, said venturi tube having an inspiration orifice, an expiration orifice, and a central orifice positioned therebetween positioned at said tube constricted portion;

a flow sensor positioned within said venturi tube to provide air flow data on the respiratory air flowing through said venturi tube;

a flow direction housing attached to said venturi tube exterior thereof, said housing having a channel with an inspiration portion, an expiration portion and a central portion positioned therebetween, said housing further including an inspiration opening providing communication between said tube inspiration orifice and an end portion of said inspiration channel portion spaced away from said central channel portion, an expiration opening providing communication between said tube expiration orifice and an end portion of said expiration channel portion spaced away from said central channel portion, and a central opening providing communication between said tube central orifice and said central channel portion to cause a flow of a portion of the respiratory air which the patient inspires to pass from said second open end of said venturi tube through said tube inspiration orifice and said housing inspiration opening and to flow through said inspiration channel portion to said housing central opening and said tube central orifice for return to said venturi tube at said tube constricted portion, and a flow of a portion of the respiratory air which the patient expires to pass from said first open end of said venturi tube through said tube expiration orifice and said housing expiration opening and to flow through said expiration channel portion to said housing central opening and said tube central orifice for return to said venturi tube at said tube constricted portion; and an inspiration air flow direction sensor positioned in said inspiration channel portion and having an output responsive to said flow of said portion of the respiratory air through said inspiration channel portion, and an expiration air flow direction sensor positioned in said expiration channel portion and having an output responsive to said flow of said portion of the respiratory air through said expiration channel portion, said outputs of said inspiration and expiration air flow direction sensors being indicative of whether the respiratory air flowing through said venturi tube is inspired air or expired air.

16. The respiratory air sensing device according to claim 15 wherein said inspiration air flow direction sensor provides an inspiration temperature signal, and said expiration air flow direction sensor provides an expiration temperature signal, and wherein said inspiration temperature signal and said expiration temperature signal are indicative of whether the respiratory air flowing through said venturi tube is inspired or expired air.

17. The respiratory air sensing device according to claim 16, further including an electronic device electrically coupled to said inspiration air flow direction sensor and said expiration air flow direction sensor to use said inspiration temperature signal and said expiration temperature signal to determine whether the respiratory air flowing through said venturi tube is inspired or expired air.

18. The respiratory air sensing device according to claim 15 wherein said flow sensor is an air mass sensor that produces an air mass indication signal.

19. The respiratory air sensing device according to claim 18 further including an air temperature sensor positioned within said venturi tube to produce an air temperature indication signal.

20. The respiratory air sensing device according to claim 19, further including a humidity sensor to detect the humidity of the ambient air outside said venturi tube and produce a humidity indication signal, and a pressure sensor to detect the pressure of the ambient air outside said venturi tube and produce a pressure indication signal, and further including an electronic device electrically coupled to said flow sensor, said air temperature sensor, said humidity sensor and said pressure sensor to use said air mass indication signal, said temperature indication signal, said humidity indication signal and said pressure indication signal to determine the volume of said respiratory air flowing through said venturi tube.

21. The respiratory air sensing device according to claim 19 further including a display, and an electronic device electrically coupled to said flow sensor and said air temperature sensor to use said air mass indication signal and said temperature indication signal to determine the volume of said respiratory air flowing through said venturi tube, said electronic device further using said temperature indication signal when corresponding to the respiratory air flowing through said venturi tube which is expired air to determine an estimated body core temperature of the patient, and providing said estimated body core temperature to said display for display thereon.

22. The respiratory air sensing device according to claim 15 wherein said flow sensor is held in position within said venturi tube by a plug positioned in said housing central opening, said plug having an air passage therethrough communicating with said central channel portion and said tube constricted portion.

23. The respiratory air sensing device according to claim 15 wherein said housing includes an outward housing portion having said channel formed on an inward face thereof, and an inward housing portion positioned between said venturi tube and said outward housing portion, said inward housing portion having an inward face and an outward face with said housing inspiration opening, said housing expiration opening and said housing central opening extending fully between said inward and outward faces of said inward housing portion, said inward housing portion having said inward face thereof sealingly mounted to said venturi tube and said outward housing portion having said inward face thereof sealingly mounted to said outward face of said inward housing portion with said channel overlaying said housing inspiration, expiration and central openings of said inward housing portion.

24. The respiratory air sensing device according to claim 23 wherein said flow sensor is held in position within said venturi tube by a plug positioned in said housing central opening, said plug having an air passage therethrough communicating with said central channel portion and said tube constricted portion, said plug being sealingly mounted in said housing central opening of said inward housing portion and sealingly engages said venturi tube about said tube central orifice to provide a seal between said venturi tube and said inward housing portion.

25. The respiratory air sensing device according to claim 23 wherein said housing inspiration opening and said housing expiration openings of said inward housing portion are tapered having a first portion thereof toward said venturi tube for communication with said tube inspiration and expiration orifices, and a second portion thereof narrower than said first portion toward said outward face of said inward housing portion for communication with said channel.

26. The respiratory air sensing device according to claim 23 further including a circuit board electrically coupled to said flow sensor, and said inspiration and expiration air flow direction sensors, and wherein said outward housing portion has a chamber formed in an outward face thereof, outward of said channel, sized to received said circuit board therein.

27. The respiratory air sensing device according to claim 15 further including a sample container and a conduit coupling said sample container to said channel to allow a flow of a portion of said respiratory air in said channel into said sample container.

28. The respiratory air sensing device according to claim 15 wherein said central channel portion is divided to define an inspiration central channel portion and an expiration central channel portion, and said housing central opening includes an inspiration central opening providing communication between said tube central orifice and said inspiration central channel portion and an expiration central opening providing communication between said tube central orifice and said expiration central channel portion.

29. A device for sensing the respiratory air of a patient, comprising:

a venturi tube including a first open end through which the patient inspires and expires, a second open end, and a constricted portion therebetween, said venturi tube having an inspiration orifice, an expiration orifice, and a central orifice positioned therebetween positioned at said tube constricted portion;

a flow sensor positioned within said venturi tube to provide air flow data on the respiratory air flowing through said venturi tube;

a conduit with an inspiration portion, an expiration portion and a central portion positioned therebetween, said conduit having an inspiration opening providing communication between said tube inspiration orifice and an end portion of said inspiration conduit portion spaced away from said central conduit portion, an expiration opening providing communication between said tube expiration orifice and an end portion of said expiration conduit portion spaced away from said central conduit portion, and a central opening providing communication between said tube central orifice and said central conduit portion to cause a flow of a portion of the respiratory air which the patient inspires to pass from said second open end of said venturi tube through said tube inspiration orifice and said conduit inspiration opening and to flow through said inspiration conduit portion to said conduit central opening and said tube central orifice for return to said venturi tube at said tube constricted portion, and a flow of a portion of the respiratory air which the patient expires to pass from said first open end of said venturi tube through said tube expiration orifice and said conduit expiration opening and to flow through said expiration conduit portion to said conduit central opening and said tube central orifice for return to said venturi tube at said tube constricted portion; and an inspiration air flow direction sensor positioned in said inspiration conduit portion and having an output responsive to said flow of said portion of the respiratory air through said inspiration conduit portion, and an expiration air flow direction sensor positioned in said expiration conduit portion and having an output responsive to said flow of said portion of the respiratory air through said expiration conduit portion, wherein the respiratory air flowing through said venturi tube can be determined to be inspired air or expired air from said outputs of said inspiration and expiration air flow direction sensors.

30. The respiratory air sensing device according to claim 29 wherein said inspiration air flow direction sensor provides an inspiration temperature signal, and said expiration air flow direction sensor provides an expiration temperature signal, and wherein said inspiration temperature signal and said expiration temperature signal are indicative of whether the respiratory air flowing through said venturi tube is inspired or expired air.

31. The respiratory air sensing device according to claim 30, further including an electronic device electrically coupled to said inspiration air flow direction sensor and said expiration air flow direction sensor to use said inspiration temperature signal and said expiration temperature signal to determine whether the respiratory air flowing through said venturi tube is inspired or expired air.

32. The respiratory air sensing device according to claim 29 wherein said flow sensor is an air mass sensor that produces an air mass indication signal.

33. The respiratory air sensing device according to claim 32 further including an air temperature sensor positioned within said venturi tube to produce an air temperature indication signal.

34. The respiratory air sensing device according to claim 33, further including a humidity sensor to detect the humidity of the ambient air outside said venturi tube and produce a humidity indication signal, and a pressure sensor to detect the pressure of the ambient air outside said venturi tube and produce a pressure indication signal, and further including an electronic device electrically coupled to said flow sensor, said air temperature sensor, said humidity sensor and said pressure sensor to use said air mass indication signal, said temperature indication signal, said humidity indication signal and said pressure indication signal to determine the volume of said respiratory air flowing through said venturi tube.

35. The respiratory air sensing device according to claim 33 further including a display, and an electronic device electrically coupled to said flow sensor and said air temperature sensor to use said air mass indication signal and said temperature indication signal to determine the volume of said respiratory air flowing through said venturi tube, said electronic device further using said temperature indication signal when corresponding to the respiratory air flowing through said venturi tube which is expired air to determine an estimated body core temperature of the patient, and providing said estimated body core temperature to said display for display thereon.

36. The respiratory air sensing device according to claim 29 wherein said flow sensor is held in position within said venturi tube by a plug positioned in said conduit central opening, said plug having an air passage therethrough communicating with said central conduit portion and said tube constricted portion.

37. The respiratory air sensing device according to claim 29, further including a housing with an outward housing portion having a channel formed on an inward face thereof to define said conduit, and an inward housing portion positioned between said venturi tube and said outward housing portion, said inward housing portion having an inward face and an outward face with said conduit inspiration opening, said conduit expiration opening and said conduit central opening extending fully between said inward and outward faces of said inward housing portion, said inward housing portion having said inward face thereof sealingly mounted to said venturi tube and said outward housing portion having said inward face thereof sealingly mounted to said outward face of said inward housing portion with said channel overlaying said conduit inspiration, expiration and central openings of said inward housing portion.

38. The respiratory air sensing device according to claim 37 wherein said flow sensor is held in position within said venturi tube by a plug positioned in said conduit central opening, said plug having an air passage therethrough communicating with said central channel portion and said tube constricted portion, said plug being sealingly mounted in said conduit central opening of said inward housing portion and sealingly engaging said venturi tube about said tube central orifice to provide a seal between said venturi tube and said inward housing portion.

39. The respiratory air sensing device according to claim 29 further including a sample container in communication with said conduit to allow a flow of a portion of said respiratory air in said conduit into said sample container.

40. The respiratory air sensing device according to claim 29 for use in the respiratory passageway of a patient, further including a flexible tube having a first end portion sized to be positioned in the respiratory passageway and a second end portion connected to said venturi tube at said first open end.

41. The respiratory air sensing device according to claim 40 wherein said second end portion of said flexible tube is removably connected to said venturi tube at said first open end.

42. The respiratory air sensing device according to claim 29 for use in the respiratory passageway of a patient wherein said conduit is formed in a sidewall of said venturi tube toward said first open end, and said sidewall is sized to be positioned in the respiratory passageway.

43. The respiratory air sensing device according to claim 29 wherein said central conduit portion includes an inspiration conduit central portion communicating with said inspiration conduit portion and an expiration conduit central portion communicating with said expiration conduit portion, said inspiration and expiration conduit central portions providing separate paths of air flow, and said conduit central opening including an inspiration central opening providing communication between said tube central orifice and said inspiration conduit central portion and an expiration central opening providing communication between said tube central orifice and said expiration conduit central portion, said inspiration and expiration central openings providing separate paths of air flow to said tube central orifice.

44. A device for sensing the direction of flow of a gas, comprising:

a venturi tube including a first open end, a second open end, and a constricted midportion therebetween, the gas being able to flow in a first direction from said first open end to said second open end and in a second direction from said second open end to said first open end, said venturi tube having a first orifice, a second orifice, and a central orifice positioned therebetween at said tube midportion;

a flow direction housing attached to said venturi tube exterior thereof, said housing having a channel with a first portion, a second portion and a central portion positioned therebetween, said housing further including a first opening aligned with said tube first orifice and in communication with an end portion of said first channel portion spaced away from said central channel portion, a second opening aligned with said tube second orifice and in communication with an end portion of said second channel portion spaced away from said central channel portion, and a central opening aligned with said tube central orifice and in communication with said central channel portion to cause a flow of a portion of the gas flowing in said first direction to pass from said first open end of said venturi tube through said tube first orifice and said housing first opening and to flow through said first channel portion to said housing central opening and said tube central orifice for return to said venturi tube at said tube midportion, and a flow of a portion of the gas flowing in said second direction to pass from said second open end of said venturi tube through said tube second orifice and said housing second opening and to flow through said second channel portion to said housing central opening and said tube central orifice for return to said venturi tube at said tube midportion; and a first gas flow direction sensor positioned in said first channel portion and having an output responsive to said flow of said portion of the gas through said first channel portion, and a second gas flow direction sensor positioned in said second channel portion and having an output responsive to said flow of said portion of the gas through said second channel portion, wherein the gas flowing through said venturi tube can be determined to be flowing in said first or second direction by comparing said outputs of said first and second gas flow direction sensors.

45. The gas flow sensing device according to claim 44 wherein said first gas flow direction sensor is a thermistor positioned in said first channel portion and providing a first temperature signal, and said second gas flow direction sensor is a thermistor positioned in said second channel portion and providing a second temperature signal, and wherein the signal strength of said first temperature signal relative to the signal strength of said second temperature signal is indicative of whether the gas flowing through said venturi tube is in said first or second direction.

46. The gas flow sensing device according to claim 44 further including a gas mass sensor positioned within said tube midportion to produce a gas mass indication signal for the gas flowing through said venturi tube.

47. The gas flow sensing device according to claim 46 further including a gas temperature sensor positioned within said tube midportion to produce a gas temperature indication signal.

48. The gas flow sensing device according to claim 47, further including a microprocessor receiving and using said gas mass indication signal and said temperature indication signal to determine the volume of the gas flowing through said venturi tube.

49. The gas flow sensing device according to claim 46 wherein said gas mass sensor is held in position within said tube midportion by a plug, said plug being positioned in said tube central orifice and said housing central opening, and has a gas passage therethrough communicating with said central channel portion and said tube midportion.

50. The gas flow sensing device according to claim 49 wherein said plug is sealingly mounted in said tube central orifice and said housing central orifice to provide a seal between said venturi tube and said housing.

51. The gas flow sensing device according to claim 44, wherein said housing includes an outward housing portion having said channel formed on an inward face thereof, and an inward housing portion positioned between said venturi tube and said outward housing portion, said inward housing portion having an inward face and an outward face with said housing first opening, said housing second opening and said housing central opening extending fully between said inward and outward faces of said inward housing portion, said inward housing portion having said inward face thereof sealingly mounted to said venturi tube and said outward housing portion having said inward face thereof sealingly mounted to said outward face of said inward housing portion with said channel overlaying said housing first, second and central openings of said inward housing portion.

52. The gas flow sensing device according to claim 51 wherein said housing first opening and said housing second openings of said inward housing portion are tapered having a first portion thereof toward said venturi tube for communication with said tube first and second orifices, and a second portion thereof narrower than said first portion toward said outward face of said inward housing portion for communication with said channel.

53. The gas flow sensing device according to claim 51 further including a circuit board electrically coupled to said first and second gas flow direction sensors, and wherein said outward housing portion has a chamber formed in an outward face thereof, outward of said channel, sized to received said circuit board therein.

54. The gas flow sensing device according to claim 44 wherein said central channel portion includes a first central channel portion and a second central channel portion, and said housing central opening includes a first central opening providing communication between said tube central orifice and said first central channel portion and a second central opening providing communication between said tube central orifice and said second central channel portion, said first central channel portion and said first central opening providing a first path of gas flow to said venturi tube and said second central channel portion and said second central opening providing a second path of gas flow to said venturi tube, said first and second paths being separate.

55. A device for sensing the direction of flow of a gas, comprising:

a venturi tube including a first open end, a second open end, and a constricted portion therebetween, the gas being able to flow in a first direction from said first open end to said second open end and in a second direction from said second open end to said first open end, said venturi tube having a first orifice, a second orifice, and a central orifice positioned at said tube constructed portion therebetween;

a conduit with a first portion, a second portion and a central portion positioned therebetween, said conduit having a first opening providing communication between said tube first orifice and an end portion of said first conduit portion spaced away from said central conduit portion, a second opening providing communication between said tube second orifice and an end portion of said second conduit portion spaced away from said central conduit portion, and a central opening providing communication between said tube central orifice and said central conduit portion to cause a flow of a portion of the gas flowing in said first direction to pass from said first open end of said venturi tube through said tube first orifice and said conduit first opening and to flow through said first conduit portion to said conduit central opening and said tube central orifice for return to said venturi tube at said tube constricted portion, and a flow of a portion of the gas flowing in said second direction to pass from said second open end of said venturi tube through said tube second orifice and said conduit second opening and to flow through said second conduit portion to said conduit central opening and said tube central orifice for return to said venturi tube at said tube constricted portion; and a first gas flow direction sensor positioned in said first conduit portion and having an output responsive to said flow of said portion of the gas through said first conduit portion, and a second gas flow direction sensor positioned in said second conduit portion and having an output responsive to said flow of said portion of the gas through said second conduit portion, wherein the gas flowing through said venturi tube can be determined to be flowing in said first or second direction from said outputs of said first and second gas flow direction sensors.

56. The gas flow sensing device according to claim 55 wherein said first gas flow direction sensor provides a first temperature signal, and said second gas flow direction sensor provides a second temperature signal, and wherein said first temperature signal and said second temperature signal are indicative of whether the gas flowing through said venturi tube is in said first or second direction.

57. The gas flow sensing device according to claim 56, further including an electronic device electrically coupled to said first gas flow direction sensor and said second gas flow direction sensor to use said first temperature signal and said second temperature signal to determine whether the gas flowing through said venturi tube is in said first or second direction.

58. The gas flow sensing device according to claim 55, further including a gas sensor positioned within said venturi tube to produce a gas mass indication signal for the gas flowing through said venturi tube.

59. The gas flow sensing device according to claim 58 wherein said gas mass sensor is held in position within said venturi tube by a plug positioned in said conduit central opening, said plug having a gas passage therethrough communicating with said central conduit portion and said tube constricted portion.

60. The gas flow sensing device according to claim 55, further including a housing with an outward housing portion having a channel formed on an inward face thereof to define said conduit, and an inward housing portion positioned between said venturi tube and said outward housing portion, said inward housing portion having an inward face and an outward face with said conduit first opening, said conduit second opening and said conduit central opening extending fully between said inward and outward faces of said inward housing portion, said inward housing portion having said inward face thereof sealingly mounted to said venturi tube and said outward housing portion having said inward face thereof sealingly mounted to said outward face of said inward housing portion with said channel overlaying said conduit first, second and central openings of said inward housing portion.

61. The gas flow sensing device according to claim 55 wherein said central conduit portion includes a first conduit central portion and a second conduit central portion, said first conduit central portion providing communication between said first conduit portion and said tube central orifice, and said second conduit central channel portion providing communication between said second conduit portion and said tube central orifice, said first conduit central portion providing a first path of gas flow to said venturi tube and said second conduit central portion providing a second path of gas flow to said venturi tube, said first and second paths being separate.

62. A device for sensing the direction of flow of a gas, comprising:

a venturi tube including a first open end, a second open end, and a constricted midportion therebetween, the gas being able to flow in a first direction from said first open end to said second open end and in a second direction from said second open end to said first open end, said venturi tube having a first orifice positioned toward said first open end and a central orifice positioned at said tube midportion;

a gas flow sensor positioned within said venturi tube to provide a tube gas flow signal indicating gas is flowing through said venturi tube;

a flow direction housing attached to said venturi tube exterior thereof, said housing having a first opening aligned with said tube first orifice and a central opening aligned with said tube central orifice, said housing further including a channel extending between said housing first opening and said housing central opening to cause a flow of a portion of the gas flowing in said first direction to pass from said first open end of said venturi tube through said tube first orifice and said housing first opening and to flow through said channel to said housing central opening and said tube central orifice for return to said venturi tube at said tube midportion;

a first gas flow direction sensor positioned in said channel and producing a channel gas flow signal indicating gas is flowing through said channel, wherein said first gas flow direction sensor indicates that gas is flowing through said venturi tube in said first direction; and an electronic device receiving said tube gas flow signal and said channel gas flow signal, and determining that the gas is flowing through said venturi tube in said second direction based on the lack of said channel gas flow signal indicating flow in said channel indicative of flow in said venturi tube in said first direction as sensed by said first gas flow direction sensor and the indication of gas flow in said venturi tube by said tube gas flow signal as sensed by said tube gas flow sensor.

63. The gas flow sensing device according to claim 62 wherein said flow sensor is a gas mass sensor that produces a gas mass indication signal.

64. The gas flow sensing device according to claim 62 wherein said electronic device is a microprocessor.

65. The gas flow device according to claim 62 wherein said flow sensor is held in position within said tube midportion by a plug, said plug being positioned in said tube central orifice and said housing central opening, and having a gas passage therethrough communicating with said channel and said tube midportion.

66. The gas flow sensing device according to claim 65 wherein said plug is sealingly mounted in said tube central orifice and said housing central orifice to provide a seal between said venturi tube and said housing.

67. The gas flow sensing device according to claim 62, wherein said housing includes an outward housing portion having said channel formed on an inward face thereof, and an inward housing portion positioned between said venturi tube and said outward housing portion, said inward housing portion having an inward face and an outward face with said housing first opening and said housing central opening extending fully between said inward and outward faces of said inward housing portion, said inward housing portion having said inward face thereof sealingly mounted to said venturi tube and said outward housing portion having said inward face thereof sealingly mounted to said outward face of said inward housing portion with said channel overlaying said housing first and central openings of said inward housing portion.

68. The gas flow sensing device according to claim 67 wherein said housing first opening of said inward housing portion is tapered having a first portion thereof toward said venturi tube for communication with said tube first orifice, and a second portion thereof narrower than said first portion toward said outward face of said inward housing portion for communication with said channel.

69. The gas flow sensing device according to claim 67 further including a circuit board electrically coupled to said flow sensor and said first gas flow direction sensor, and wherein said outward housing portion has a chamber formed in an outward face thereof, outward of said channel, sized to received said circuit board therein.

70. A device for sensing the direction of flow of a gas, comprising:

a venturi tube including a first open end, a second open end, and a constricted portion therebetween, the gas being able to flow in a first direction from said first open end to said second end and in a second direction from said second open end to said first open end, said venturi tube having a first orifice positioned toward said first open end and a central orifice positioned at said tube constricted portion;

a gas mass flow sensor positioned within said venturi tube to provide a tube gas flow signal indicating gas is flowing through said venturi tube;

a conduit extending between said tube first orifice and said tube central orifice to cause a flow of a portion of the gas flowing in said first direction to pass from said first open end of said venturi tube through said tube first orifice and said conduit to said tube central orifice for return to said venturi tube at said tube constricted portion;

a first gas flow direction sensor positioned in said conduit and producing a conduit gas flow signal indicating gas is flowing through said conduit, wherein said first gas flow direction sensor indicates that gas is flowing through said venturi tube in said first direction; and an electronic device receiving said tube gas flow signal and said conduit gas flow signal, and determining that the gas is flowing through said venturi tube in said second direction based on the lack of said conduit gas flow signal indicating flow in said conduit as sensed by said first gas flow direction sensor and the indication of gas flow in said venturi tube by said tube gas flow signal as sensed by said tube gas flow sensor.

71. The gas flow sensing device according to claim 70 for use in the respiratory passageway of a patient, further including a flexible tube having a first end portion sized to be positioned in the respiratory passageway and a second end portion connected to said venturi tube at said first open end.

72. The gas flow sensing device according to claim 71 wherein said second end of portion of said flexible tube is removably connected to said venturi tube at said first open end.

73. The gas flow sensing device according to claim 70 for use in the respiratory passageway of a patient, wherein said conduit is formed in a sidewall of said venturi tube toward said first open end, and said sidewall is sized to be positioned in the respiratory passageway.

74. A device for sensing the respiratory air of a patient, comprising:

a venturi tube including a first open end through which the patient inspires and expires, a second open end, and a constricted portion therebetween, said venturi tube having an inspiration orifice and an expiration orifice;

a flow sensor positioned within said venturi tube to provide air flow data on the respiratory air flowing through said venturi tube;

a conduit with an inspiration portion, an expiration portion and a central portion positioned therebetween, said conduit having an inspiration opening providing communication between said tube inspiration orifice and an end portion of said inspiration conduit portion spaced away from said central conduit portion, an expiration opening providing communication between said tube expiration orifice and an end portion of said expiration conduit portion spaced away from said central conduit portion, and a central opening providing communication between a location exterior of said venturi tube and said central conduit portion to cause a flow of a portion of the respiratory air which the patient inspires to pass from said second open end of said venturi tube through said tube inspiration orifice and said conduit inspiration opening and to flow through said inspiration conduit portion to said conduit central opening for delivery to said location exterior of said venturi tube, and a flow of a portion of the respiratory air which the patient expires to pass from said first open end of said venturi tube through said tube expiration orifice and said conduit expiration opening and to flow through said expiration conduit portion to said conduit central opening for delivery to said location exterior of said venturi tube; and an inspiration air flow direction sensor positioned in said inspiration conduit portion and having an output responsive to said flow of said portion of the respiratory air through said inspiration conduit portion, and an expiration air flow direction sensor positioned in said expiration conduit portion and having an output responsive to said flow of said portion of the respiratory air through said expiration conduit portion, wherein the respiratory air flowing through said venturi tube can be determined to be inspired air or expired air from said outputs of said inspiration and expiration air flow direction sensors.

75. The respiratory air sensing device according to claim 74 wherein said flow sensor is an air mass sensor that produces an air mass indication signal.

76. The respiratory air sensing device according to claim 75 further including an air temperature sensor positioned within said venturi tube to produce an air temperature indication signal.

77. The respiratory air sensing device according to claim 76, further including a humidity sensor to detect the humidity of the ambient air outside said venturi tube and produce a humidity indication signal, and a pressure sensor to detect the pressure of the ambient air outside said venturi tube and produce a pressure indication signal, and further including an electronic device electrically coupled to said flow sensor, said air temperature sensor, said humidity sensor and said pressure sensor to use said air mass indication signal, said temperature indication signal, said humidity indication signal and said pressure indication signal to determine the volume of said respiratory air flowing through said venturi tube.

78. The respiratory air sensing device according to claim 74 wherein said venturi tube further includes a central orifice positioned between said tube inspiration and expiration orifices, and said flow sensor is held in position within said venturi tube by a plug positioned in said conduit central opening.

79. The respiratory air sensing device according to claim 74, further including a housing with an outward housing portion having a channel formed on an inward face thereof to define said conduit, and an inward housing portion positioned between said venturi tube and said outward housing portion, said inward housing portion having an inward face and an outward face with said conduit inspiration opening and said conduit expiration opening extending fully between said inward and outward faces of said inward housing portion, said inward housing portion having said inward face thereof sealingly mounted to said venturi tube and said outward housing portion having said inward face thereof sealingly mounted to said outward face of said inward housing portion with said channel overlaying said conduit inspiration and expiration openings of said inward housing portion.

80. The respiratory air sensing device according to claim 79 wherein said conduit central opening extends through said housing and terminates in an exterior port such that said location exterior of said venturi tube is exterior of said housing, and further including a sample container in communication with said external port to allow a flow of a portion of said respiratory air in said conduit into said sample container.

81. The respiratory air sensing device according to claim 80 further including a removable closure selectively positionable at said tube second open end to increase the pressure within said venturi tube upon the patient expiring air into said first open end.

* * * * *